United States Patent [19]

Busse et al.

[11] 4,370,322

[45] Jan. 25, 1983

[54] TOPICALLY ADMINISTRABLE PHARMACEUTICAL COMPOSITIONS CONTAINING ANTI-INFLAMMATORY STEROIDS

[75] Inventors: Michael J. Busse, Harrow; Kenneth A. Lees, Northwood, both of England

[73] Assignee: Glaxo Group Limited, London, England

[21] Appl. No.: 308,581

[22] Filed: Oct. 5, 1981

[30] Foreign Application Priority Data

Oct. 6, 1980 [GB] United Kingdom ................. 8032111

[51] Int. Cl.³ ............................................. A61K 31/56
[52] U.S. Cl. .................................................. 424/243
[58] Field of Search .................... 424/243; 260/397.45

[56] References Cited

U.S. PATENT DOCUMENTS 3,856,828 12/1974 Phillipps et al. .................... 424/243
4,070,462 1/1978 Ecker ................................. 424/243

Primary Examiner—Elbert L. Roberts
Attorney, Agent, or Firm—Bacon & Thomas

[57] ABSTRACT

Pharmaceutical compositions such as ointments and creams are provided by admixture of anti-inflammatory steroids active on topical application with a liquid oily phase containing at least one oil possessing a viscosity less than 10 centistokes and in which the steroid has a solubility of at least 0.5% by weight at 25° C., the degree of unsaturation of the steroid in the liquid oily phase of the composition at 25° C., being at least 3. Examples of steroids which may be used are betamethasone, beclomethasone and clobetasol derivatives. Suitable oils include esters of mono- and dibasic aliphatic acids. The compositions may include further oils such as liquid paraffin and conventional additives used in the preparation of ointments and creams. The local anti-inflammatory effect of the steroids is maintained in such formulations but systemic side effects are decreased.

14 Claims, No Drawings

TOPICALLY ADMINISTRABLE PHARMACEUTICAL COMPOSITIONS CONTAINING ANTI-INFLAMMATORY STEROIDS

The present invention relates to novel pharmaceutical compositions containing anti-inflammatory steroids.

Anti-inflammatory steroids such as clobetasol 17-propionate are commonly formulated for topical application in solution in relatively polar solvents such as propylene glycol which, in the case of ointments, may be dispersed in white soft paraffin. Such formulations permit some penetration of the active steroid into the skin to exert a topical anti-inflammatory effect. It is thought to be particularly important that the steroid should not, however, be so completely absorbed that it can exert a systemic effect which would be likely to lead to the various unwanted side effects observed with anti-inflammatory steroids such as cortisol suppression.

The use of isopropyl and butyl adipates as well as of ethyl lactate and ethanol as vehicles for the topical formulation of triamcinolone acetonide and its dicoumaryl ester is described in a paper by Altmeyer and Zaun in Arch. Derm. Forsch 1974, 248, 387–390. The effects of these vehicles on the vasoconstrictor properties of the compounds is discussed, and it is concluded that the base in which a corticosteroid is administered determines to a great extent its penetration rate, strength and duration of topical anti-inflammatory activity. There is no discussion, however, of the possible dangers of enhanced penetration in increasing systemic absorption. As far as can be determined, the solutions of triamcinolone acetonide concerned were saturated or even supersaturated which we believe would have tended to maximise release of the steroid into the aqueous body fluids.

We have now found that the systemic side effects produced by anti-inflammatory steroids on topical administration can be significantly decreased if they are applied in solution in certain oils, provided that the degree of unsaturation of the steroid in the oil is relatively high, but that the local anti-inflammatory effect and clinical efficacy of the steroids are not correspondingly reduced. Consequently, it is possible to apply about the same amount of the steroid to achieve the same local anti-inflammatory effect but to correspondingly reduce unwanted systemic effects.

The formulations according to the invention comprise an anti-inflammatory steroid dissolved in a liquid oily phase as defined hereinafter. The quantity of the liquid oily phase in relation to the quantity of steroid and the solubility of the steroid in the liquid oily phase have been found to be particularly important: the solution of the steroid in the liquid oily phase of the composition should be not more than one third saturated at 25° C., i.e. have a degree of unsaturation at 25° C. of at least 3. This means that the quantity of the liquid oily phase present should be sufficient to dissolve, at 25° C., at least three times the amount of steroid which is actually present.

Thus, according to the present invention we provide pharmaceutical compositions comprising an anti-inflammatory steroid active on topical application dissolved in a liquid oily phase containing at least one oil possessing a viscosity less than 10 centistokes and in which the steroid has a solubility of at least 0.5% by weight at 25° C., the degree of unsaturation of the steroid in the liquid oily phase of the composition at 25° C. being at least 3.

Examples of steroids which can benefit by this type of formulation are Beclomethasone 17,21-dipropionate, Betamethasone 17-valerate, Betamethasone 17,21-dipropionate, Clobetasol 17-propionate, Clobetasone 17-butyrate and chloromethyl 17α-acetoxy-9α-fluoro-11β-hydroxy-16β-methyl-3-oxoandrosta-1,4-diene-17β-carboxylate.

Formulations containing betamethasone 17-valerate, beclomethasone 17,21-dipropionate and clobetasol 17-propionate are preferred. Formulations containing clobetasol 17-propionate are particularly preferred since incidence of dermal atrophy has been shown to be significantly reduced in healthy volunteers when this formulation is used.

Suitable oils for inclusion as solvents for the steroids include esters of mono- and dibasic aliphatic acids, such esters having, for example, 6 to 18 carbon atoms, such as the butyl and isopropyl esters of adipic, lauric, palmitic and myristic acids. Dibutyl adipate is particularly useful. Mixtures of the above esters can also be employed.

The compositions according to the invention may contain a mixture of the solvent oil with one or more further oils in which the steroid is soluble and/or one or more oils in which the steroid is substantially insoluble, such as hydrocarbon oils, e.g. liquid paraffin. The liquid paraffin can either be the standard, relatively viscous kind (viscosity about 100 centistokes) or may more advantageously be a light paraffin having a much lower viscosity, for example about 7 centistokes. Use of such light liquid paraffin improves the penetration of the liquid oily phase into the skin.

It will be appreciated that when the principal solvent oil, such as dibutyl adipate, is present in admixture with a non-solvent oil such as a hydrocarbon, the solubility of the steroid in the liquid oily phase will not be a linear function of the concentration of the solvent oil in the mixture. The solubility of the chosen active steroid in any mixture of solvent and non-solvent oils can readily be determined by experiment.

The following Tables illustrate typical solubility values, at 25° C., of various steroids in various mixtures of solvents.

TABLE I

| Mixture: dibutyl adipate + liquid paraffin | |
|---|---|
| % dibutyl adipate in mixture | % solubility of Clobetasol 17-propionate in mixture |
| 25 | 0.025 |
| 28 | 0.07 |
| 36 | 0.22 |
| 50 | 0.45 |
| 65 | 0.65 |
| 75 | 1.2 |
| 85 | 1.5 |
| 100 | 1.9 |

TABLE II

Mixture A: dibutyl adipate + isopropyl myristate
Mixture B: dibutyl adipate + liquid paraffin

| % dibutyl adipate in mixture (A or B) | % solubility of Clobetasone 17-butyrate in mixture | |
|---|---|---|
| | A | B |
| 0 | 0.65 | 0.02 |
| 10 | 0.70 | — |
| 20 | 1.02 | 0.08 |
| 30 | 1.6 | 0.15 |
| 40 | 2.1 | 0.45 |

TABLE II-continued

Mixture A: dibutyl adipate + isopropyl myristate
Mixture B: dibutyl adipate + liquid paraffin

| % dibutyl adipate in mixture (A or B) | % solubility of Clobetasone 17-butyrate in mixture | |
|---|---|---|
| | A | B |
| 50 | 2.55 | 0.8 |
| 60 | 2.95 | 2.0 |
| 70 | 3.5 | 2.75 |

TABLE III

Mixture: diisopropyl adipate + liquid paraffin

| % diisopropyl adipate in mixture | % solubility in mixture of: | |
|---|---|---|
| | Clobetasone 17-butyrate | Clobetasol 17-propionate |
| 25 | 0.15 | 0.095 |
| 50 | 2.45 | 0.75 |
| 65 | 2.85 | 1.25 |
| 75 | 2.95 | 1.45 |
| 85 | 4.4 | 2.1 |
| 100 | 7.0 | 3.0 |

Table IV shows the solubility of betamethasone 17-valerate at 25° C. in two solvent oils:

TABLE IV

| Solvent Oil | % Solubility of Betamethasone 17-valerate |
|---|---|
| Dibutyl adipate | 0.9 |
| Diisopropyl adipate | 1.4 |

The degree of unsaturation appears to be particularly important in relation to the absence of systemic side effects, and while it should be above 3 it is not necessary for the degree of unsaturation to exceed about 5.0, although higher values may not be disadvantageous.

The concentrations of the active steroids in the formulations according to the invention are conveniently in the range 0.02% to 0.5%, e.g. 0.05% to 0.25% by weight, although higher percentages e.g. up to 1.5% may be employed. Preferably the compositions contain 0.05% to 0.50% by weight of active steriod.

The compositions of the invention may, for example, take the form of ointments or creams. In ointments, solid wax will commonly be present. Such an ointment may, for example, contain 55 to 90% by weight of liquid phase and 10-45% of solid wax, more usually 65-80% by weight liquid phase and 20-35% by weight of solid wax. Cream formulations will normally be emulsions, commonly oil-in-water or water-in-oil emulsions, containing 10-80%, more usually 20-60%, by weight of oil phase. Such creams can also contain emulsifying agents, which may be surfactants or emulsifying waxes, for example, cetostearyl alcohol, Cetomacrogol 1000 or self-emulsifying monostearin, as well as preservatives, buffers, stabilisers etc.

The foregoing formulations for topical application to the skin may be used for the treatment of inflammatory dermatoses of humans and animals, for example eczema, which are normally responsive to corticosteroid therapy, and also of less responsive conditions such as psoriasis in humans. The preparations may be administered by one or more applications per day to the affected area; over skin areas occlusive dressings may often be used with advantage.

The following examples are given by way of illustration only:

EXAMPLE 1

| Ointment | % w/w |
|---|---|
| Clobetasol 17-propionate | 0.05 |
| Dibutyl adipate | 25.00 |
| Microcrystalline Wax 140/145 | 30.00 |
| Liquid paraffin BP | to 100.00 |

The ointment formulation in Example 1 contains 0.07% of clobetasol 17-propionate in its liquid oily phase (dibutyl adipate+liquid paraffin). As can be seen from the solubility values in Table 1 above, to dissolve that level of clobetasol 17-propionate requires 28% of dibutyl adipate in the liquid oily phase. The liquid oily phase in fact contains about 36% of dibutyl adipate which as indicated in Table 1 is sufficient to dissolve 0.22% of clobetasol 17-propionate, i.e. more than 3 times the amount of steroid which is actually present in the formulation. Similarly the formulations of Examples 2-10 may be arrived at from the solubility values given in the tables or else the values may be determined by experiment.

EXAMPLE 2

| Ointment | % w/w |
|---|---|
| Clobetasol 17-propionate | 0.05 |
| Dibutyl adipate | 40 |
| Beeswax | 15 |
| Isopropyl myristate | to 100 |

EXAMPLE 3

| Ointment | % w/w |
|---|---|
| Clobetasone 17-butyrate | 0.1 |
| Microcrystalline was 140/145 | 40.0 |
| Dibutyl adipate | 25.0 |
| Ultra light liquid paraffin | to 100.0 |

EXAMPLE 4

| Cream | % w/w |
|---|---|
| Clobetasol 17-propionate | 0.05 |
| Dibutyl adipate | 30.0 |
| Microcrystalline wax 140/145 | 7.5 |
| Cetostearyl alcohol | 7.5 |
| Cetomacrogol 1000 | 1.0 |
| Sodium citrate | 0.05 |
| Citric acid | 0.05 |
| Chlorocresol | 0.1 |
| Water | to 100.0 |

EXAMPLE 5

| Cream | % w/w |
|---|---|
| Clobetasol 17-propionate | 0.05 |
| Dibutyl adipate | 50.0 |
| Beeswax | 7.0 |
| Cetostearyl alcohol | 7.0 |
| Self-emulsifying monstearin | 2.0 |
| Sodium citrate | 0.05 |
| Citric acid | 0.05 |
| Chlorocresol | 0.1 |
| Water | to 100.0 |

EXAMPLE 6

| Ointment | % w/w |
|---|---|
| Betamethasone 17-valerate | 0.12 |
| Dibutyl adipate | 60 |
| Microcrystalline Wax 140/145 | 20 |
| Beeswax | 10 |
| Liquid paraffin | to 100 |

EXAMPLE 7

| Ointment | % w/w |
|---|---|
| Beclomethasone 17,21-dipropionate | 0.025 |
| Dibutyl adipate | 37.5 |
| Microcrystalline Wax 140/145 | 30 |
| Liquid paraffin | to 100 |

EXAMPLE 8

| Cream-like ointment | % w/w |
|---|---|
| Clobetasol 17-propionate | 0.05 |
| Dibutyl adipate | 22.0 |
| Microcrystalline Wax 140/145 | 30.0 |
| Beeswax | 3.0 |
| Cetomacrogol 1000 | 3.0 |
| Titanium dioxide | 2.0 |
| Ultra-light liquid paraffin | to 100.0 |

EXAMPLE 9

| Ointment | % w/w |
|---|---|
| Chloromethyl 17α-acetoxy-9α-fluoro-11β-hydroxy-16β-methyl-3-oxoandrosta-1,4-diene-17β-carboxylate | 0.1 |
| Dibutyl adipate | 84.9 |
| Beeswax | 15.0 |

EXAMPLE 10

| Ointment | % w/w |
|---|---|
| Betamethasone 17,21-dipropionate | 0.05 |
| Beeswax | 10.00 |
| Microcrystalline wax 140/145 | 20.00 |
| Dibutyl adipate | to 100.00 |

The method used for making up the formulations is as follows: the steroid is dissolved in a portion of or all of the dibutyl adipate. The other ingredients are mixed together at 60°–70° C. and the steroid solution added to the mixture which is then stirred and cooled until semi-solid.

We claim:

1. A pharmaceutical composition comprising an anti-inflammatory steroid selected from beclomethasone 17,21-dipropionate, betamethasone 17-valerate, betamethasone 17,21-dipropionate, clobetasol 17-propionate, clobetasone 17-butyrate and chloromethyl 17α-acetoxy-9α-fluoro-11β-hydroxy-16β-methyl-3-oxoandrosta-1,4-diene-17β-carboxylate dissolved in a liquid oily phase containing at least one oil possessing a viscosity less than 10 centistokes and in which the steroid has a solubility of at least 0.5% by weight at 25° C., the degree of unsaturation of the steroid in the liquid oily phase of the composition at 25° C. being at least 3.

2. A pharmaceutical composition according to claim 1 wherein the liquid oily phase contains at least one oil selected from the esters of mono- and dibasic aliphatic acids, the said esters having from 6 to 18 carbon atoms.

3. A pharmaceutical composition according to claim 2 wherein the liquid oily phase contains at least one oil selected from the butyl and isopropyl esters of adipic, lauric, palmitic and myristic acids.

4. A pharmaceutical composition according to claim 3 wherein the liquid oily phase contains dibutyl adipate.

5. A pharmaceutical composition according to claim 4 which contains clobetasol 17-propionate.

6. A pharmaceutical composition according to claim 4 which contains betamethasone 17-valerate.

7. A pharmaceutical composition according to claim 4 which contains beclomethasone 17,21-dipropionate.

8. A pharmaceutical composition according to claim 1 wherein the liquid oily phase contains further oils.

9. A pharmaceutical composition according to claim 8 wherein the liquid oily phase contains liquid paraffin having a viscosity of about 7 centistokes.

10. A pharmaceutical composition according to claim 1 wherein the degree of unsaturation of the steroid is in the range 3.0 to 5.0.

11. A pharmaceutical composition according to claim 1 wherein the concentration of the steroid is from 0.02 to 1.5% by weight of the composition.

12. A pharmaceutical composition according to claim 1 in the form of an ointment or cream.

13. A pharmaceutical composition according to claim 12 containing, as additional ingredients, substances selected from solid wax, emulsifying agents, preservatives, buffers, stabilisers and other conventional additives.

14. A method of treatment of inflammatory dermatoses of humans and animals comprising topically administering to the affected skin a pharmaceutical composition according to claim 1.

* * * * *

UNITED STATES PATENT AND TRADEMARK OFFICE
CERTIFICATE OF CORRECTION

PATENT NO. : 4,370,322

DATED : January 25, 1983

INVENTOR(S) : BUSSE et al

It is certified that error appears in the above—identified patent and that said Letters Patent is hereby corrected as shown below:

Column 2, line 19, change "6 to 18" to --6 to 20--.

Claim 2, line 4, change "6 to 18" to --6 to 20--.

Signed and Sealed this

Thirty-first Day of May 1983

[SEAL]

Attest:

DONALD J. QUIGG

Attesting Officer    Acting Commissioner of Patents and Trademarks